US008419702B2

(12) United States Patent
Shimizu et al.

(10) Patent No.: US 8,419,702 B2
(45) Date of Patent: Apr. 16, 2013

(54) DISPOSABLE DIAPER PROVIDED WITH TAPE FASTENER

(75) Inventors: Jyoji Shimizu, Kagawa (JP); Osamu Nakajima, Kagawa (JP); Tomoko Sugito, Kagawa (JP); Kyo Kikuchi, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 759 days.

(21) Appl. No.: 12/449,337

(22) PCT Filed: Dec. 14, 2007

(86) PCT No.: PCT/JP2007/074094
§ 371 (c)(1),
(2), (4) Date: Jan. 19, 2010

(87) PCT Pub. No.: WO2008/096505
PCT Pub. Date: Aug. 14, 2008

(65) Prior Publication Data
US 2010/0211038 A1    Aug. 19, 2010

(30) Foreign Application Priority Data

Feb. 7, 2007  (JP) .................................. 2007-28210

(51) Int. Cl.
*A61F 13/58* (2006.01)
*A61F 13/62* (2006.01)

(52) U.S. Cl.
USPC ............................ 604/389; 604/391; 604/387

(58) Field of Classification Search ................... 604/389, 604/391
See application file for complete search history.

(56) References Cited

U.S. PATENT DOCUMENTS

| 3,995,639 | A | * | 12/1976 | Cheslow ........................ 604/390 |
| 4,010,754 | A | * | 3/1977 | Pieniak ......................... 604/390 |
| 4,209,016 | A | * | 6/1980 | Schaar .......................... 604/390 |
| 4,826,499 | A | * | 5/1989 | Ahr ............................... 604/389 |
| 4,850,988 | A | * | 7/1989 | Aledo et al. ............. 604/385.21 |
| 4,911,702 | A | * | 3/1990 | O'Leary et al. ............... 604/389 |
| 5,358,500 | A | * | 10/1994 | Lavon et al. ............ 604/385.29 |
| 5,383,871 | A | * | 1/1995 | Carlin et al. ............ 604/385.29 |
| 5,399,219 | A | * | 3/1995 | Roessler et al. .............. 156/259 |
| 5,482,588 | A | * | 1/1996 | Goulait et al. ............... 156/264 |
| 5,496,298 | A | * | 3/1996 | Kuepper et al. .............. 604/389 |
| 5,554,144 | A | * | 9/1996 | Roe et al. .................. 604/385.3 |
| 5,560,798 | A | * | 10/1996 | Brusky .......................... 156/277 |
| 5,603,794 | A | * | 2/1997 | Thomas ....................... 156/256 |
| 5,669,897 | A | * | 9/1997 | Lavon et al. ............ 604/385.24 |
| 5,873,870 | A | * | 2/1999 | Seitz et al. ............... 604/385.04 |
| 5,899,895 | A | * | 5/1999 | Robles et al. ............ 604/385.29 |

(Continued)

FOREIGN PATENT DOCUMENTS

| JP | 3-104326 | 10/1991 |
| JP | 03104326 U | * 10/1991 |

(Continued)

*Primary Examiner* — Susan Su
(74) *Attorney, Agent, or Firm* — Brinks Hofer Gilson & Lione

(57) ABSTRACT

The present invention aims to improve the tape fasteners provided on the diaper chassis so that the upper outside regions of the wearer's thighs should not be irritated by the edges of the tape fasteners. A lower edge of a first section in each tape fastener extends so that a space is defined between this lower edge and an imaginary extension of a lower edge of a second section in the tape fastener.

11 Claims, 5 Drawing Sheets

U.S. PATENT DOCUMENTS

| | | | |
|---|---|---|---|
| 5,906,008 A * | 5/1999 | Heki et al. .................... 2/400 |
| 6,004,306 A * | 12/1999 | Robles et al. ............ 604/385.21 |
| 6,454,752 B1 | 9/2002 | Huang et al. |
| 7,850,670 B2 * | 12/2010 | Reyes ...................... 604/385.03 |
| 2002/0107498 A1 | 8/2002 | Kling et al. |
| 2003/0109844 A1* | 6/2003 | Gibbs .......................... 604/389 |
| 2006/0089616 A1* | 4/2006 | Belau et al. ................... 604/389 |
| 2006/0129121 A1* | 6/2006 | Erdman ........................ 604/389 |
| 2007/0142815 A1* | 6/2007 | Macura et al. ................ 604/389 |
| 2007/0234529 A1* | 10/2007 | Middlesworth et al. ........ 24/442 |
| 2009/0264853 A1* | 10/2009 | Miyamoto et al. ............ 604/389 |
| 2010/0004616 A1* | 1/2010 | Nakamura et al. ............ 604/389 |
| 2010/0057035 A1* | 3/2010 | Putzer et al. .............. 604/385.16 |
| 2012/0035579 A1* | 2/2012 | Miyamoto et al. ............ 604/391 |
| 2012/0101469 A1* | 4/2012 | Sperl ............................ 604/391 |

FOREIGN PATENT DOCUMENTS

| | | |
|---|---|---|
| JP | 08-317950 | 12/1996 |
| JP | 09-038139 | 2/1997 |
| JP | 2003-14490 | 5/2003 |
| JP | 2003-533247 | 11/2003 |
| JP | 2004-515316 | 5/2004 |

* cited by examiner (a)

(b)

DISPOSABLE DIAPER PROVIDED WITH TAPE FASTENER

RELATED APPLICATIONS

The present application is a 35 U.S.C. §371 national stage filing of International Patent Application No. PCT/JP2007/074094, filed Dec. 14, 2007, to which priority is claimed under 35 U.S.C. §120 and through which priority is claimed under 35 U.S.C. §119 to Japanese Priority Patent Application No. 2007-28210, filed Feb. 7, 2007.

TECHNICAL FIELD

The present invention relates to a disposable diaper provided with tape fasteners used to connect front and rear waist regions of the diaper to each other.

RELATED ART

Disposable diapers provided with the tape fasteners used to connect the front and rear waist regions of the diapers chassis each other have conventionally been well known. For example, PATENT DOCUMENT 1 discloses the tape fasteners 110 (See FIG. 5(a)) comprising the first sections 111 fixed to the opposite side edges of the rear waist region in the diaper chassis and the second section 112 having the fastening means attached thereon adapted to be detachably fastened to the front waist region wherein both the first section 111 and the second section 112 integrally extend laterally of the diaper chassis. Furthermore, PATENT DOCUMENT 2 discloses the tape fasteners 210 (See FIG. 5(b)) comprising a first section 211 fixed to the rear waist region in the diaper chassis so as to be relatively long in the vertical direction and the second section 212 extending laterally from the middle region of the first section 211 and adapted to be detachably fastened to the landing sheet strip 219 bonded to the front waist region in the diaper chassis wherein the second section 212 forms together with the first section 211 a square convex.
PATENT DOCUMENT 1: JP 08-317950 A
PATENT DOCUMENT 2: JP 09-38139 A

DISCLOSURE OF THE INVENTION

Problem to be Solved by the Invention

Infants, predominant users of diapers, often briskly move legs and/or crawl on hands and knees with diapers put thereon. In such situation, with the disposable diaper of prior art using the tape fasteners 110, 210 as disclosed in PATENT DOCUMENTS 1 and 2, each of lower edges 111A, 211A of the first sections 111, 211 located on the opposite side edges of the waist region inevitably comes in contact with the wearer's thigh 130 in upper outside region 130a thereof and consequently the wearer's skin might not only experience uncomfortable feeling but also be damaged and even suffer from inflammation. This is for the reason that such tape fasteners of prior art have the respective edges defined by cut edges along which the tape fasteners have been cut from a common sheet material having a higher stiffness than those of the other soft components of the diaper chassis and thus the edges (i.e., cut edges) of such stiff tape fasteners irritate delicate skin of the infant, predominant user of the disposable diaper.

Certainly it may be contemplated, for example, to put the attachment location of the tape fastener on the rear waist region aside upward to solve the problem. However, the attachment location of the tape fastener is substantially predetermined for the purpose of properly putting the diaper on the wearer's body. In view of this, it is undesirable to put aside arbitrarily the attachment location of the diaper on the rear waist region upward.

It is an object of the present invention to solve the problem as has been described above and the other objects of the invention will be more fully understood from the description given hereunder.

Measure to Solve the Problem

The problem as has been described above is solved, according to the present invention, by an improvement in a disposable diaper having a longitudinal axis and a transverse axis and comprising a diaper chassis and tape fasteners wherein said diaper chassis is contoured by first and second ends opposed to each other in a direction defined by the longitudinal axis and extending in a direction defined by the transverse axis and first and second side edges opposed to each other in the direction defined by the transverse axis and extending in the direction defined by the longitudinal axis and having first and second waist regions opposed to each other by intermediary of a crotch region, and wherein each of said tape fasteners is used to connect the first and second waist regions with each other and including first and second sections being contiguous to each other wherein each of the first and second sections has upper edge (11b, 12b) and lower edge (11a, 12a) opposed to each other in the direction defined by the longitudinal axis and an imaginary center line extending in a lengthwise direction of the tape fastener and bisecting a width of said tape fastener between the upper and lower edges, wherein the first section is fixed to at least the first side edge of the first and second side edges in the first waist region and the second section extends from the first side edge in the direction defined by the transverse axis so that the imaginary center line extends in parallel to the transverse axis and wherein the second section is provided on its inner surface with a fastening strip.

The improvement according to the present invention is characterized in that the first section of the tape fastener is angularly deviated from the second section toward the first end of the first waist region so that a space is defined between the lower edge of the first section and an imaginary extension of the lower edge of the second section extending toward the longitudinal axis.

The present invention comprises the other preferred embodiments as will be described below.

An embodiment in which the lower edge of the first section in the tape fastener obliquely ascends toward the first end as the lower edge traces from the first side edge of the diaper chassis toward the longitudinal axis.

An embodiment in which the lower edge of the first section describes at least one circular arc.

An embodiment in which the circular arc is convex or concave.

An embodiment in which the circular arc comprises alternate concave and convex circular arcs being contiguous one to another along said lower edge of said first section in a lengthwise direction of the first section.

An embodiment in which dimensions of the first section and the second section as measured in the direction defined by the longitudinal axis are substantially same and an area of the first section is larger than an area of the fastening strip provided on the second section.

An embodiment in which the second section has a finger-grip tab extending outward from the fastening strip in the direction defined by the transverse axis.

An embodiment in which the first section is sandwiched between layers of a laminate member containing fibrous nonwoven fabric forming a skin-contacting side wherein said laminate member constitutes the diaper chassis.

An embodiment in which the fastening strip comprises a plurality of hooks or loops for so-called mechanical fastener or a layer of pressure-sensitive adhesive.

In the description, the first waist region should be understood as one of front and rear waist regions and the second waist region should be understood as the other of these front and rear waist regions.

Effect of the Invention

The tape fastener according to the present invention is characterized in that the lower edge of the first section is angularly deviated from the lower edge of the second section toward the first end (e.g., the upper end) of the first waist region (e.g., the rear waist region) so that the space is defined between the lower edge of the first section and the imaginary extension of the lower edge in the second section extending toward the longitudinal axis. Therefore, even when the second section is located in the same zone of the first waist region as in the conventional diaper, the upper outside region of the wearer's thigh would not come in contact with the lower edge of the first section in the tape fastener due to brisk movement of the wearer's leg. Consequentially, the lower edge of the first section would not give the wearer uncomfortable feeling and/or break the wearer's skin and/or give any irritation to the wearer's skin which is sometimes leading to inflammation. In this way, the object of the present invention is achieved.

Figure 1:
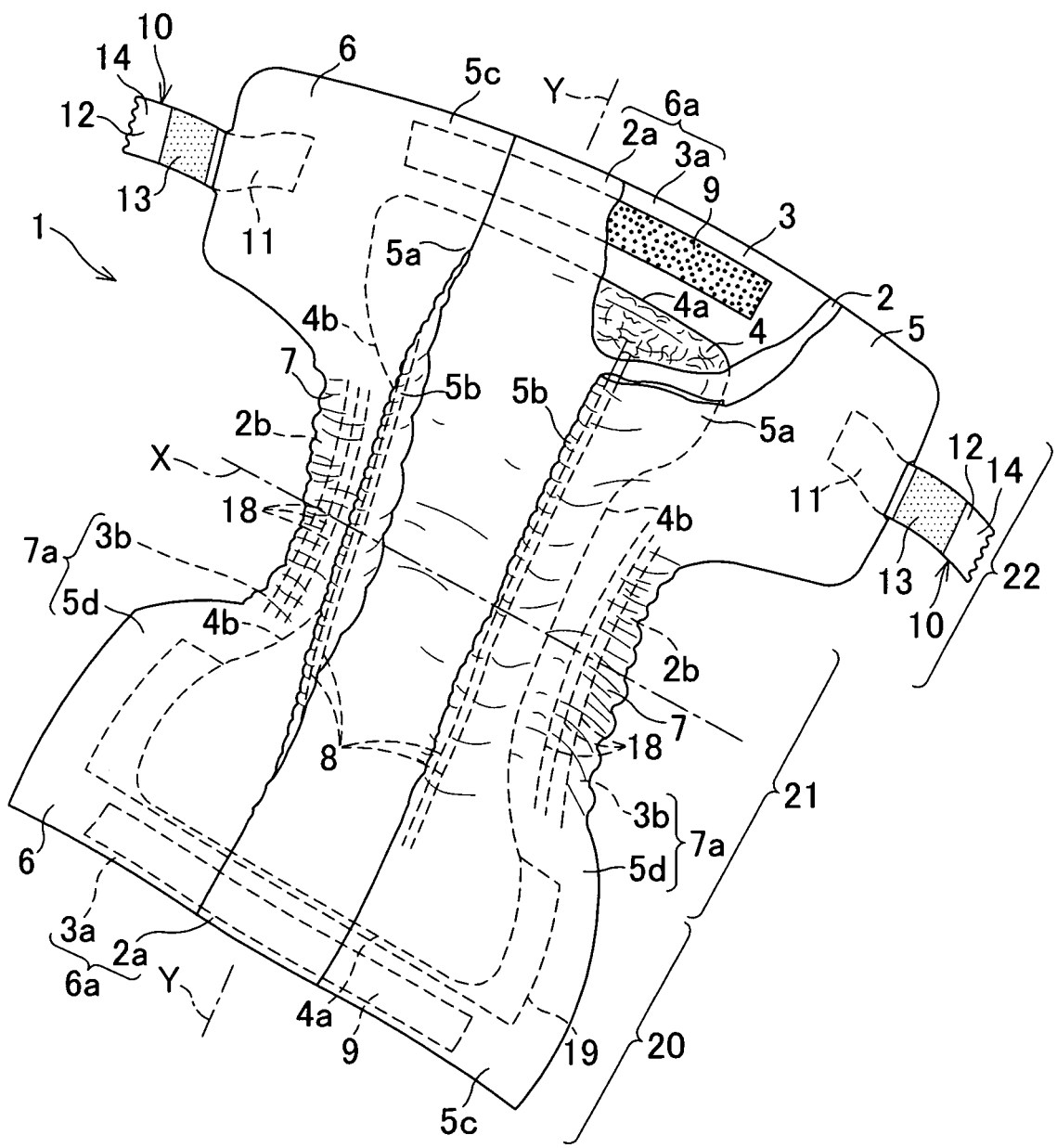
FIG. 1 is a partially cutaway plan view showing a disposable diaper as viewed from a skin-contact surface thereof.

IDENTIFICATION OF REFERENCE NUMERALS USED IN THE DRAWINGS 1 diaper chassis
6 end of chassis
7 side edge of chassis
10 tape fastener
11 first section
11a lower edge of first section
11b upper edge of first section
12 second section
12a lower edge of second section
12b upper edge of second section
13 fastening strip
14 finger-grip tab
Y longitudinal axis
X transverse axis
C center line of tape fastener
N imaginary extension
S space

DETAILED DESCRIPTION OF THE PREFERRED EMBODIMENTS

Fig. 1 is a partially cutaway plan view showing a disposable diaper according to the present invention as viewed from an inner surface thereof. A diaper chassis 1 basically comprises a liquid-pervious inner sheet 2 made of fibrous nonwoven fabric, perforated plastic film or a laminate thereof disposed to face the wearer's skin, a liquid-impervious outer sheet 3 made of moisture-pervious plastic film, fibrous nonwoven fabric or a laminate thereof disposed to face away from the wearer's skin, a liquid-absorbent core 4 typically made of a mixture of fluff pulp and super-absorbent polymer particles sandwiched and fixed between the inner and outer sheets 2, 3 and a pair of sheet-like liquid-barrier cuffs 5 made of fibrous nonwoven fabric or the like and disposed on upper surface of the inner sheet 2 along opposite side edges thereof.

The diaper chassis 1 comprises a front waist region 20, a rear waist region 22 and a crotch region 21 extending between these front and rear waist regions 20, 22 and contoured by both ends 6 opposed to each other in a direction defined by longitudinal axis Y and extending in a direction defined by transverse axis X together with both side edges 7 opposed to each other in the direction defined by the transverse axis and extending in the direction defined by the longitudinal axis Y. The opposite side edges 7 in the crotch region 21 are curved inward so that the crotch region 21 may properly fit the wearer's body along thighs thereof.

Each of the liquid-barrier cuffs 5 comprises a proximal edge portion 5a extending in the direction defined by the longitudinal axis Y immediately outside of one of opposite side edges 4b of the liquid-absorbent core 4 and fixed to the diaper chassis 1 in the vicinity of the side edge 4b, a distal edge portion 5b put aside from the proximal edge 5a inward (toward the longitudinal axis Y) and having an inner periphery folded back, end portions 5c opposite in the direction defined by the longitudinal axis Y and a side flap defining region 5d extending outward from the proximal edge portion 5a toward one of the opposite side edges 7 of the diaper chassis 1. The distal edge portion 5b contains therein an elastic member 8 extending in its lengthwise direction and attached thereto under tension so that the distal edge portion 5b is spaced upward from the inner sheet 2 as the elastic member 8 contracts.

Along both of the ends 6 of the diaper chassis 1, opposite ends 2a of the inner sheet 2 extending outward beyond opposite ends 4a of the liquid-absorbent core 4 in the direction defined by the longitudinal axis Y and opposite ends 3a of the outer sheet 3 are put flat and bonded together to form end flaps 6a, respectively, containing therein tape-shaped waist elastic members 9 extending in its lengthwise direction and bonded to these end flaps 6a. In the respective end flaps 6a, the end portions 5c of the liquid-barrier cuff 5 are bonded to the upper surface of the inner sheet 2.

Along the opposite side edges 7 of the diaper chassis 1, the opposite side edges 2b of the inner sheet 2 extend in the direction defined by the transverse axis X beyond opposite side edges 4b of the liquid-absorbent core 4 while the opposite side edges 3b of the outer sheet 3 and the side flap defining regions 5d further extend in the same direction beyond the opposite side edges 2b so that these components are bonded together to form a pair of side flaps 7a. In the crotch region 21, the side flaps 7a respectively contain therein a plurality of leg elastic members 18 extending circumferentially with respect to the respective legs and bonded thereto under tension. The opposite side edges 2b of the inner sheet 2 are fixed between the opposite side edges 3b of the outer sheet 3 and the side flap defining regions 5d of the liquid-barrier cuffs 5.

The diaper includes a pair of tape fasteners 10 attached to both of the side edges 7 of the rear waist region 22, respectively. Alternatively, it is possible to attach one of these tape fasteners 10 to at least one of the side edges 7 of the rear waist region 22 with the other side edge 7 of the rear waist region 22 previously connected to the associated side edge 7 of the front waist region 20. In the front waist region 20, the outer sheet 3 is provided on its outer surface with an anchoring sheet strip (i.e., target tape) 19 including a plurality of loops constituting so-called mechanical fastener and defining a landing zone for the tape fastener. The tape fastener 10 is made of relatively stiff material such as plastic film, fibrous nonwoven fabric, a laminate thereof or kraft paper and comprises a first section 11 fixed to the associated one of the side flaps 7a of the rear waist region 22 and a second section 12 extending outward from the first section 11 in the direction defined by the transverse axis X beyond the associated side flap 7a. The second section 12 is provided on its inner surface with a fastening strip 13 bonded thereto wherein the fastening strip 13 has a plurality of hooks constituting the mechanical fastener adapted to be releasably engaged with a plurality of loops provided on the anchoring sheet strip 19 and a finger-grip tab 14 extends outward from the fastening strip 13 in the direction defined by the transverse axis X. As viewed in the direction defined by the longitudinal axis Y, a dimension of the first section 11 is substantially equal to a dimension of the second section 12 and an area of the first section 11 is larger than an area of the fastening strip 13. The first section 11 is sandwiched between the side edge 3b of the outer sheet 3 and the side flap defining region 5d of the liquid-barrier cuff 5. The anchoring sheet strip 19 may be replaced by the outer sheet 3 made of fibrous nonwoven fabric having a sufficiently high strength to ensure that the fastening strip 13 of the tape fastener 10 is directly and releasably fastened to the outer sheet 3.

It will be apparent from the description with no need for drawings that, depending on the diaper, the tape fasteners 10 may be attached to the front waist region 20 instead of the rear waist region 22 and, in this case, the anchoring tape strip 19 would be attached to the rear waist region 22.

Though not illustrated in the drawings, when the second section 12 of the tape fastener 10 is folded back toward the longitudinal axis Y to be temporarily fixed at the time before used and its opposed surface faces the liquid-barrier cuff 5 made of fibrous nonwoven fabric, the second section 12 is releasably fixed to this opposed surface. The fastening strip having a plurality of hooks may be replaced by pressure-sensitive adhesive. In this case, preferably, a separator coated with silicon or the like is attached to the opposed surface while plastic film having a smooth surface of releasability is bonded to the anchoring sheet strip 9.

Figure 2:
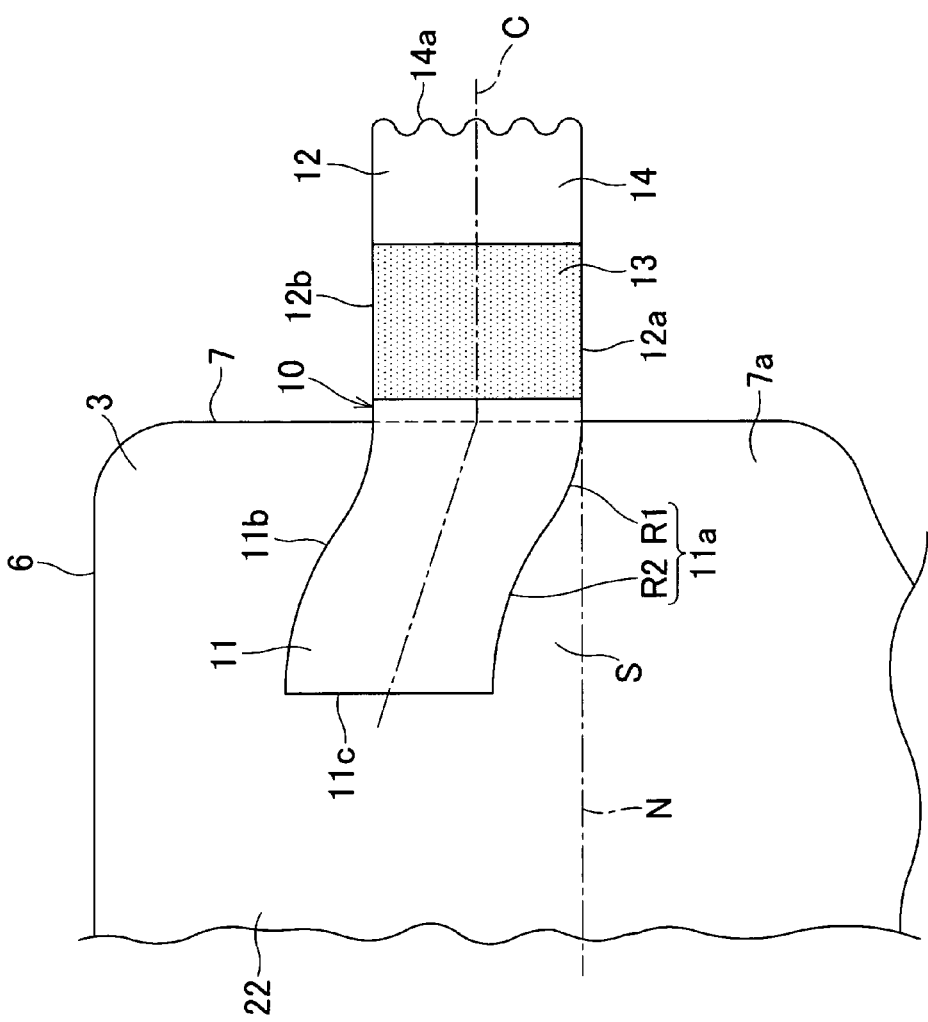
FIG. 2 is a partial side view illustrating configuration of a tape fastener and a manner in which the tape fastener is attached to the diaper.

FIG. 2 is a partial side view illustrating configuration of the tape fastener 10 and a manner in which the tape fastener 10 is attached to the diaper. The tape fastener 10 is divided in the first and second sections 11, 12 in the direction defined by the transverse axis X (See FIG. 1) with a boundary line defined by the side edge 7 of the rear waist region 22 and the tape fastener 10 as a whole is contoured by the lower edges 11a, 12a and the upper edges 11b, 12b which are substantially parallel to these lower edges 11a, 12a together with inner and outer ends 11c, 14a. Between the upper and lower edges, an imaginary centerline C is indicated to extend in a lengthwise direction of the tape fastener 10. The first section 11 extends aside from the second section 12 toward the end 6 of the rear waist region 22 so that a space S is defined between the lower end 11a of the first section 11 and an imaginary extension N of the lower edge 12a of the second section 12 extending toward the longitudinal axis Y (See FIG. 1). More specifically, the, lower edge 11a in its entirety obliquely ascends toward the end 6 of the rear waist region 22 as the lower edge 11a traces from the side edge 7 of the rear waist region 22 toward the longitudinal axis Y. Additionally, a segment in the lower edge 11a of the first section 11 extending in the vicinity of the border between the first and second sections 11, 12 describes a convex arc R1 and a segment extending from this convex arc R1 toward the inner end 11c describes a concave arc R2. It should be understood that the arc referred to herein is not required to be a circular arc defined by any specific curvature radius and may be a segment appropriately curved to protect the wearer's thigh against undesirable irritation. The second section 12 extends outward from the side edge 7 of the rear waist region 22 in the direction defined by the transverse axis X so that its imaginary center line C extends in parallel to the transverse axis X of the diaper chassis 1. The second section 12 extending in parallel to the transverse axis X in this manner allows the wearer or a helper to hold the finger-grip tab 14 without consciously ascertaining the location of the finger-grip tab 14 and thereby allowing operation of fastening to be smoothly carried out and the second section 12 would be easily fastened to the anchoring sheet strip 19 extending in a waist surrounding direction. A distal end 14a of the finger-grip tab 14 is defined by alternately arranged convex and concave circular arcs.

Figure 3:
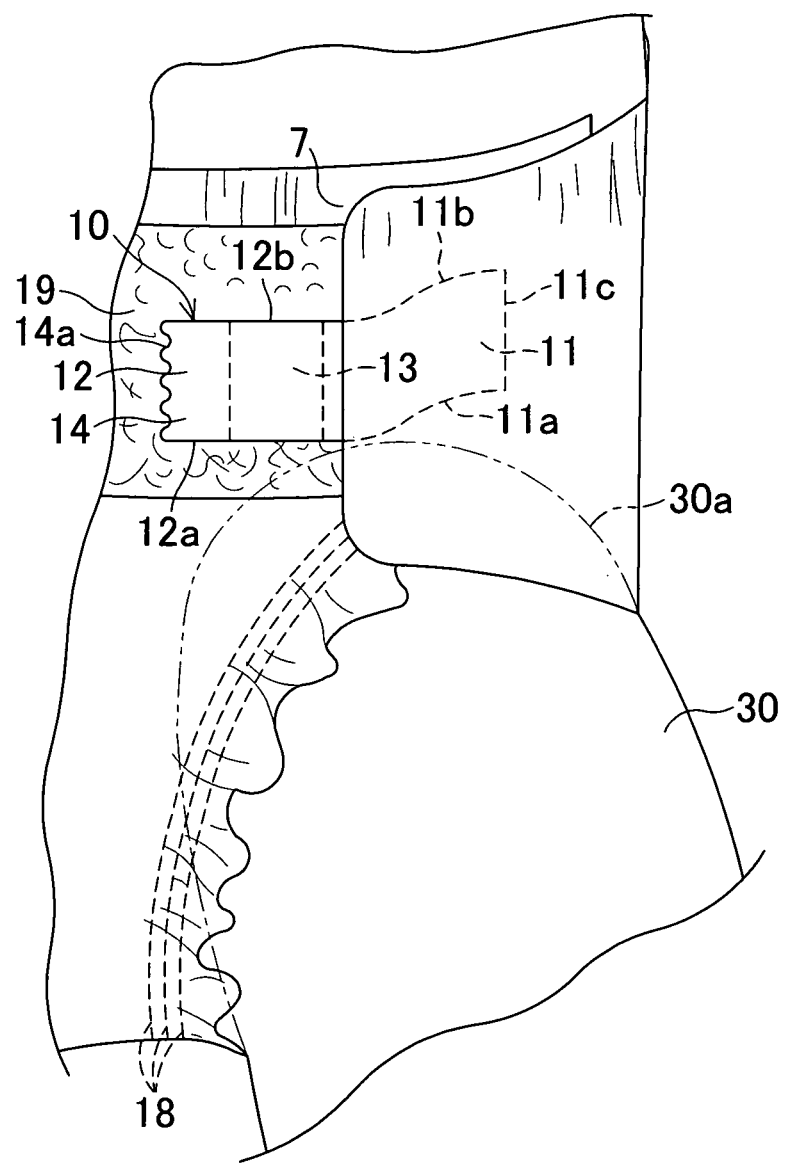
FIG. 3 is a side view illustrating a manner in which the taper fastener is used.

FIG. 3 is a side view illustrating a state in which the diaper is put on the wearer's body. The tape fastener 10 is engaged via the fastening strip 13 with the anchoring sheet strip 19 so as to define a waist-opening and a pair of leg-openings. Assumed that the diaper put on the wearer's body in a substantially proper manner, in the diaper according to the present invention using the particularly configured tape fasteners 10 as shown by FIG. 2, it is assured the upper outside region 30a of the wearer's thigh 30 lies at a level lower than the lower edge 11a of the first section 11 more or less depending on transverse dimensions of the diaper chassis 1 and the tape fastener 10 as measured in the direction defined by the longitudinal axis Y. Accordingly, the upper outside region 30a of the thigh 30 would not come in contact with the lower edge 11a of the first section 11 even when the wearer moves his or her legs unless the diaper chassis 1 is slipped down by such movement. Should the region 30a comes in contact with the lower edge 11a of the first section 11 as the diaper chassis 1 is slipped down due to movement of the wearer's legs, the lower edge 11a of the first section 11 describing a circular arc or the similar curve well alleviates the anxiety that such lower edge 11a might give the wearer uncomfortable feeling and/or break the upper outside region 30a of the diaper's thigh 30 and/or irritate hard the wearer's skin to cause inflammation.

With the diaper put on the wearer's body, the tape fasteners are exposed to various forces depending on various movements of the wearer's body. For example, the lower edge 11a and/or the upper edge 11b of the first section 11 may be exposed to the force potentially curling up or twisting these edges 11a and/or 11b and, if these edges 11a and/or 11b are in alignment with the lower edge 12a and/or the upper edge 12b of the second section 12, such curling up or twisting force might be linearly transmitted to the fastening strip 13 engaged with the anchoring sheet strip 19 so as to peel the fastening strip 13 off from the anchoring sheet strip 19.

However, such apprehension can be substantially avoided or alleviated by the tape fastener 10 according to the invention constructed so that at least the lower edge 11a of the first section 11 is not in alignment with the lower edge 12a of the second section 12. Consequentially, said force potentially curling up or twisting the edges 11a and/or 11b of the first section 11 is not directly transmitted to the fastening strip 13 and said apprehension is substantially alleviated.

When it is desired to peel the fastening strip 13 on the second section 12 of the tape fastener 10 off from the anchoring sheet strip 19, the distal end 14a of the finger-grip tab 14 may be held with the fingers. In this case, the distal end 14a of the finger-grip tab 14 defined by a plurality of alternate convex and concave circular arcs contiguous one to another advantageously facilitates such operation of peeling off. Specifically, the wearer or the helper can smoothly put one of his or her fingers on the lower surface of the distal end 14a and the other finger on the upper surface thereof to hold the distal end 14a and to move this outward away from the outer surface of the diaper chassis 1.

On the assumption that the fastening strip 13 of the tape fastener 10 comprises a plurality of hooks constituting the mechanical fastener, the diaper may be stored with the second section 12 folded back toward the longitudinal axis Y and engaged with the skin-contacting inner sheet of the diaper made of fibrous nonwoven fabric until the diaper is actually used. As it has conventionally been the case, a predetermined pressure is exerted upon the second section 12 over its entire area to engage the fastening strip 13 with the corresponding region of the skin-contacting side. The respective whole areas of the first and second sections 11, 12 linearly extend in the transverse direction. The first section 11 and the second section 12 are not identical or symmetric with each other. The fastening strip 13 carried on the second section 12 which has been folded back for storage of the diaper is opposed to the first section 11 of with an angular deviation from the first section 11 with respect to the direction of the longitudinal axis Y. As a result, the fastening strip 13 carried on the second section 12 has a region overlapping the first section 11 and a region not overlapping the first section 11 by the intermediary of the fibrous nonwoven fabric. The overlapping region is thicker (i.e., higher) and more stiff than the non-overlapping region. In the overlapping region, the fastening strip 13 carried on the second section 12 is apt to be pressed against the skin-contacting side with a relatively high pressure to result in a relatively stable engagement and, in the non-overlapping region, the fastening strip 13 is apt to be pressed against the skin-contacting side with a relatively low pressure to result in a relatively unstable engagement. The region of such relatively unstable engagement facilitates the second section 12 to be peeled off from the corresponding region of the skin-contacting side for actual use of the diaper/the tape fasteners.

When the distal end 14a of the finger-grip tab 14 is held in order to peel the second section 12 off from the skin-contacting side, the distal end 14a of the finger-grip tab 14 defined by a plurality of alternate convex and concave circular arcs contiguous one to another advantageously facilitates such operation of peeling off. Specifically, the wearer or the helper can smoothly put one of his or her fingers on the lower surface of the distal end 14a and the other finger on the upper surface thereof to hold the distal end 14a and to move this outward away from the outer surface of the diaper chassis 1.

An area of the first section 11 is dimensioned to be larger than an area of the fastening strip 13 to assure a strength at which the first section 11 is attached to the diaper chassis 1 sufficiently to avoid an anxiety that the first section 11 might fall off from the attachment region and/or the attachment region might be damaged even if a relatively high tensile force is exerted on this attachment region.

Figure 4:
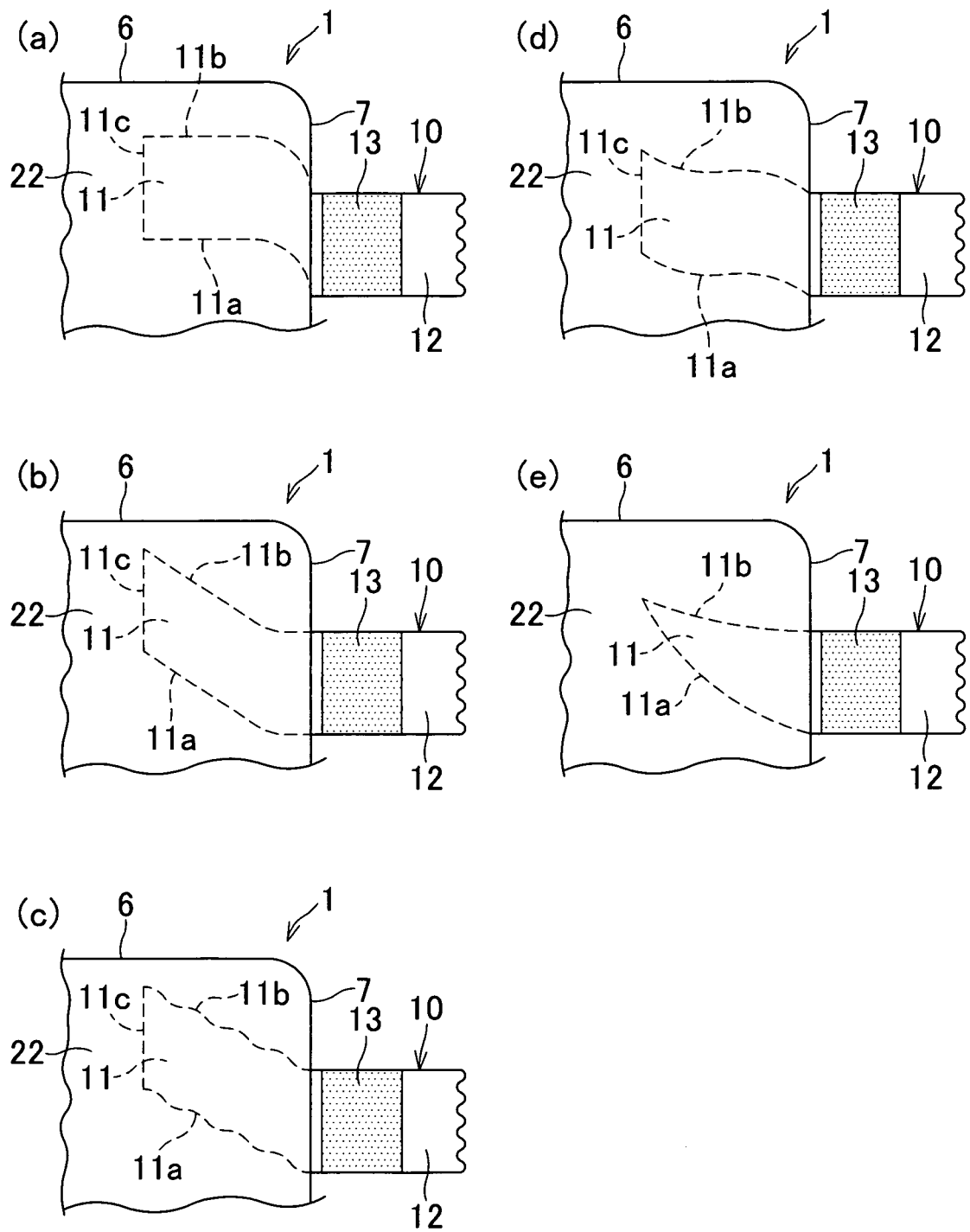
FIG. 4 is a view similar to FIG. 2 with respect to an alternative embodiment.
Figure 5:
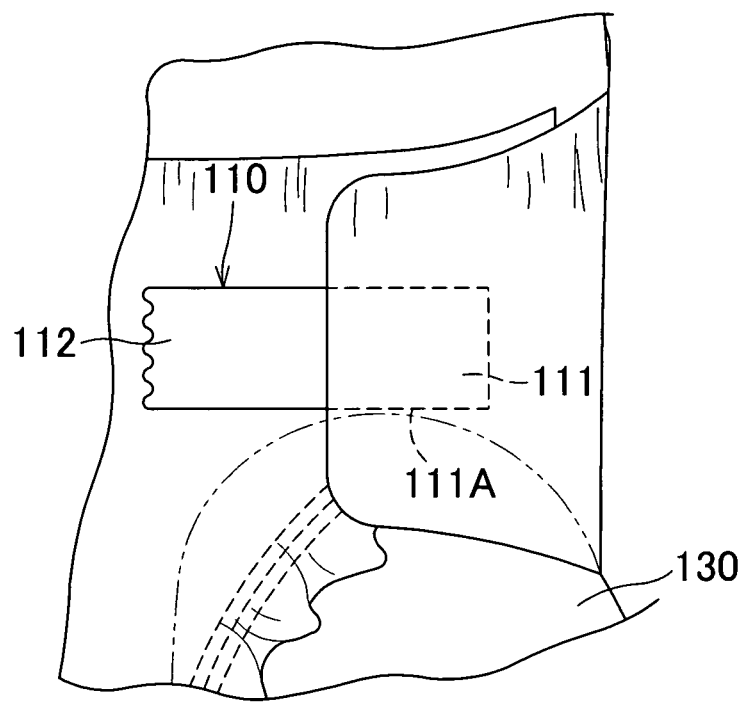
FIG. 5 is a diagram illustrating a manner in which the tape fastener of prior art is used.
Figure 5:
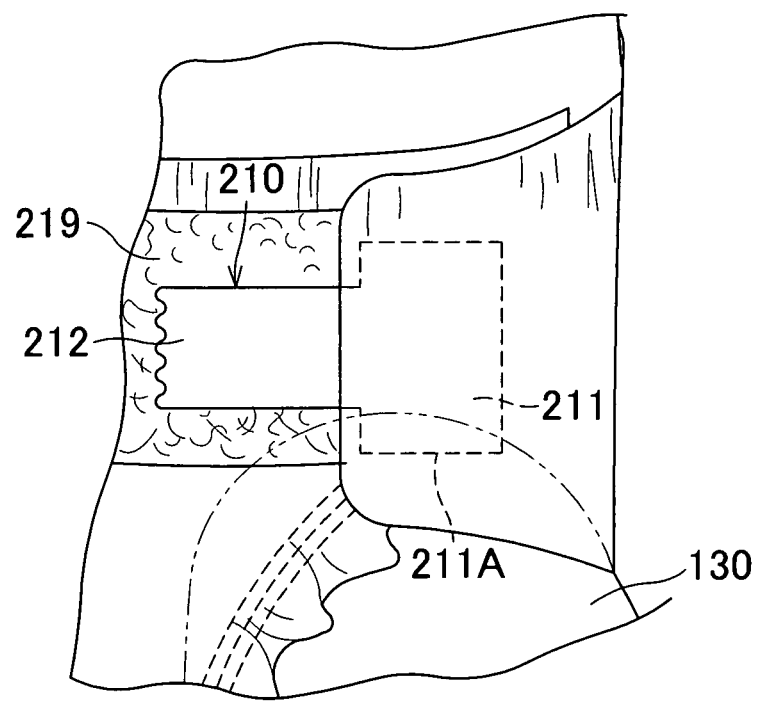

FIG. 4 shows various alternative embodiments of the tape fastener 10. The tape fasteners 10 according to these embodiments are substantially same as the previous described embodiment in basic constructions as well as in function and effect. In view of this, description of these function and effect is eliminated and description of the features different from those in the previously described embodiment will be also described as briefly as possible.

In FIG. 4(a), the first section 11 of the tape fastener 10 has the lower edge 11a and the upper edge 11b extending together from the side edge 7 of the diaper chassis 1 toward the end 6 of the diaper chassis 1 to describe convex curves followed by linearly extending toward the longitudinal axis Y substantially in parallel to each other.

In FIG. 4(b), the first section 11 of the tape fastener 10 has the lower edge 11a and the upper edge 11b are curved in the vicinity of the side edge 7 of the diaper chassis 1 toward the end 6 of the diaper chassis 1 followed by linearly extending toward the end 6.

In FIG. 4(c), the first section 11 of the tape fastener 10 has the lower edge 11a and the upper edge 11b obliquely extending upward to a plurality of alternate convex and concave circular arcs which are contiguous one to another.

In FIG. 4(d), the first section 11 of the tape fastener 10 has the lower edge 11a and the upper edge 11b convexly curved to the side toward the end 6 of the diaper chassis 1 in the vicinity of the side edge 7 of the diaper chassis 1 followed by being curved convexly to the opposite side.

In FIG. 4(e), the first section 11 of the tape fastener 10 extends inward from the side edge 7 of the diaper chassis 1 to be convexly curved toward the side opposite to the end 6 of the diaper chassis 1.

As will be understood from the embodiments as have been described above, the lower edge 11a and the upper edge 11b of the first section 11 have none of sharp regions which would irritate the wearer's skin except the inner end 11c of the first section 11. In other words, these lower and upper edges 11a, 11b are entirely defined by circular arcs. If desired, the corners of the end 11c also may be defined by circular arcs.

The invention claimed is:

1. A disposable diaper having a longitudinal axis and a transverse axis and comprising a diaper chassis having a liquid-pervious inner sheet and a liquid-impervious outer sheet, said liquid-impervious outer sheet having an outer side and an inner side that faces a wearer, and tape fasteners wherein said diaper chassis is contoured by first and second ends opposed to each other in a direction defined by said longitudinal axis and extending in a direction defined by said transverse axis and first and second side edges opposed to each other in said direction defined by said transverse axis and extending in said direction defined by said longitudinal axis and having first and second waist regions opposed to each other by intermediary of a crotch region, and wherein each of said tape fasteners is used to connect said first and second waist regions with each other and including first and second sections forming a single continuous unitary structure wherein each of said first and second sections are asymmetric to each other and each has upper edges and lower edges opposed to each other in said direction defined by said longitudinal axis and an imaginary center line extending in a lengthwise direction of said tape fastener and bisecting a width of said tape fastener between said upper and lower edges, wherein said first section is fixed to at least said first side edge of said first and second side edges in said first waist region on the inner side of the liquid-impervious outer sheet and said second section extends from said first side edge in said direction defined by said transverse axis so that said imaginary center line extends in parallel to said transverse axis and wherein said second section is provided on its inner surface with a fastening strip, said first section of said tape fastener being angularly deviated from said second section toward said first end of said first waist region so that a space is defined between said lower edge of said first section and an imaginary extension of said lower edge of said second section extending toward said longitudinal axis, wherein said lower edge of said first section in said tape fastener obliquely ascends toward said first end as said lower edge traces from said first side edge of said diaper chassis toward said longitudinal axis.

2. The diaper according to claim 1, wherein said lower edge of said first section describes at least one circular arc.

3. The diaper according to claim 2, wherein dimensions of said first section and said second section as measured in said direction defined by said longitudinal axis are substantially the same and an area of said first section is larger than an area of said fastening strip provided on said second section.

4. The diaper according to claim 2, wherein said at least one circular arc is convex or concave.

5. The diaper according to claim 4, wherein dimensions of said first section and said second section as measured in said direction defined by said longitudinal axis are substantially the same and an area of said first section is larger than an area of said fastening strip provided on said second section.

6. The diaper according to claim 2, wherein said at least one circular arc comprises alternate concave and convex circular arcs being contiguous one to another along said lower edge of said first section in a lengthwise direction of said first section.

7. The diaper according to claim 6, wherein dimensions of said first section and said second section as measured in said direction defined by said longitudinal axis are substantially the same and an area of said first section is larger than an area of said fastening strip provided on said second section.

8. The diaper according to claim 1, wherein dimensions of said first section and said second section as measured in said direction defined by said longitudinal axis are substantially the same and an area of said first section is larger than an area of said fastening strip provided on said second section.

9. The diaper according to claim 1, wherein said second section has a finger-grip tab extending outward from said fastening strip in said direction defined by said transverse axis.

10. The diaper according to claim 1, wherein said first section is sandwiched between layers of a laminate member containing fibrous nonwoven fabric forming a skin-contactable side wherein said laminate member constitutes said diaper chassis.

11. The diaper according to claim 1, wherein said fastening strip comprises a plurality of hooks or loops or a layer of pressure-sensitive adhesive.

* * * * *

UNITED STATES PATENT AND TRADEMARK OFFICE
CERTIFICATE OF CORRECTION

PATENT NO.       : 8,419,702 B2                                   Page 1 of 1
APPLICATION NO.  : 12/449337
DATED            : April 16, 2013
INVENTOR(S)      : Shimizu et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 923 days.

Signed and Sealed this
First Day of September, 2015

Michelle K. Lee
*Director of the United States Patent and Trademark Office*